US008522627B2

(12) United States Patent
Maeda

(10) Patent No.: US 8,522,627 B2
(45) Date of Patent: Sep. 3, 2013

(54) AUTOMATIC SAMPLER FOR LIQUID CHROMATOGRAPH

(75) Inventor: Yoshiaki Maeda, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 298 days.

(21) Appl. No.: 13/035,036

(22) Filed: Feb. 25, 2011

(65) Prior Publication Data

US 2011/0209532 A1 Sep. 1, 2011

(30) Foreign Application Priority Data

Feb. 26, 2010 (JP) .................................. 2010-041361

(51) Int. Cl.
*G01N 30/20* (2006.01)

(52) U.S. Cl.
USPC ........................................................ 73/863.72

(58) Field of Classification Search
None
See application file for complete search history.

(56) References Cited

U.S. PATENT DOCUMENTS 7,350,401 B2   4/2008   Takao et al.

FOREIGN PATENT DOCUMENTS

| CN | 2178285 Y | 9/1994 |
|---|---|---|
| CN | 1737372 A | 2/2006 |
| JP | 63-45471 A | 2/1988 |
| JP | 63-71650 A | 4/1988 |
| JP | 2000-104659 A | 4/2000 |
| JP | 2000-162198 A | 6/2000 |
| JP | 2003-107065 A | 4/2003 |
| JP | 2005-99056 A | 4/2005 |
| JP | 2009-276110 A | 11/2009 |

OTHER PUBLICATIONS

The First Office Action for the Application No. 201110051987.6 from The State Intellectual Property Office of the People's Republic of China dated May 30, 2013.

*Primary Examiner* — Robert R Raevis
(74) *Attorney, Agent, or Firm* — Cheng Law Group, PLLC

(57) ABSTRACT

A pump portion for taking in and discharging solutions includes a first plunger pump with a small capacity and a second plunger pump with a large capacity. Intake ports of both the plunger pumps are connected in parallel to a common port of a switching valve with a first three-way valve interposed therebetween. The first three-way valve connects the intake port of one of the plunger pumps to the switching valve. Discharge ports of both the plunger pumps are connected in parallel to one port of the switching valve with a second three-way valve interposed therebetween. The second three-way valve connects the discharge port of one of the plunger pumps to the switching valve.

6 Claims, 9 Drawing Sheets

AUTOMATIC SAMPLER FOR LIQUID CHROMATOGRAPH

BACKGROUND OF THE INVENTION

1. Field of the Invention

The present invention relates to an automatic sampler for automatically injecting a sample into an analytical flow path of a liquid chromatograph.

2. Description of Background Technique

A common automatic sampler for automatically injecting a sample into an analytical flow path of a liquid chromatograph is formed to take in a predetermined amount of a sample with a metering pump with a needle inserted in a sample vessel and to inject the taken-in sample into the liquid chromatograph (see Japanese Patent Application Laid-Open No. 2005-99056, for example).

FIG. 10 shows an example of a prior-art automatic sampler with a liquid chromatograph.

In this automatic sampler, by switching a first switching valve 8 and a second switching valve 18 and driving a needle 20, flow paths for carrying out a sample intake step, a step of introducing the sample into the liquid chromatograph, a step of cleaning the needle 20, a step of discharging a rinse solution from a cleaning port 16, and a rinse solution addition step are formed.

For example, at the time of the intake of the sample, with the needle 20 inserted into a sample vessel 15, a central common port connected to an intake port of a metering pump 5 and a port "A" are connected in the first switching valve 8 and ports "a" and "b" are connected in the second switching valve 18. As the metering pump 5, a syringe pump is used. In this state, by driving a plunger of the metering pump 5 toward a suction side, the sample is taken in from a tip end of the needle 20 and stays in a sample loop 22 provided on the flow path for connecting the port "a" of the second switching valve 18 and the needle.

At the time of the addition of a rinse solution to the cleaning port 16, after the metering pump 5 takes in any of a rinse solution "A", a rinse solution "B", and a mobile phase "C", the central common port connected to the metering pump 5 and a port "F" are connected in the first switching valve 8, and the plunger of the metering pump 5 is driven toward a discharge side, and any of the solutions is discharged to the cleaning port 16.

In the automatic sampler in FIG. 10, whether an amount of the solution, such as the sample to be injected into the liquid chromatograph, is large or small, the single metering pump 5 meters and takes in the sample. Therefore, if a metering pump 5 of a small cylinder capacity is used, an amount of the liquid which can be treated by a stroke of driving of the plunger is small. If an intake amount of the sample is small, it can be controlled with high accuracy by using a pump with such a small cylinder capacity. If the intake amount of the sample is large or at the time of intake of the rinse solution, the intake amount cannot be treated by a stroke of driving of the plunger, and it is necessary to repeat intake and discharge operations a plurality of times, which prolongs intake time of the sample or the rinse solution.

On the other hand, if a metering pump 5 of a large cylinder capacity is used, a large amount of the solution can be treated by a stroke of driving of the plunger, though accuracy of the intake amount decreases in taking in only a small amount of the sample.

In prior art, although it is possible to replace the metering pump with one with a suitable cylinder capacity according to the amount of the sample to be injected into the liquid chromatograph, it is troublesome to replace the plunger.

SUMMARY OF THE INVENTION

It is an object of the present invention to provide an automatic sampler for a liquid chromatograph capable of treating a small amount of solution with high accuracy and a large amount of solution in a short time.

The present invention is an automatic sampler for a liquid chromatograph and for taking in a sample with a plunger pump and injecting the taken-in sample into an analytical flow path of the liquid chromatograph. The automatic sampler includes, as plunger pumps, a first plunger pump and a second plunger pump having a larger cylinder capacity than the first plunger pump. Intake ports and discharge ports of both the plunger pumps are connected in parallel to a flow path switching mechanism with a pump selecting mechanism interposed therebetween. Only one of the plunger pumps is made usable to take in a solution such as the sample by switching the pump selecting mechanism.

The automatic sampler according to the invention includes: the first plunger pump for taking in the sample; the second plunger pump for taking in the sample and having the larger cylinder capacity than the first plunger pump; a sample loop for temporarily retaining the sample taken in by the first or second plunger pump; a flow path switching mechanism including a switching valve and for switching, by switching of the switching valve, between a flow path for taking the sample into the sample loop with the first or second plunger pump and a flow path for supplying the sample taken into and retained by the sample loop to an analytical flow path of the liquid chromatograph with a mobile phase; the pump selecting mechanism disposed between the intake ports and the discharge ports of both the plunger pumps and the flow path switching mechanism and for switching connection with the flow path switching mechanism so as to selectively connect one of the plunger pumps to the flow path switching mechanism, and a pump selecting means for switching the pump selecting mechanism so that the pump selecting mechanism selects the first plunger pump when an amount of the sample to be injected into the analytical flow path of the liquid chromatograph is a predetermined amount or smaller and selects the second plunger pump when the injected amount of the sample is larger than the predetermined amount.

Because only one of the first plunger pump and the second plunger pump can be used to take in the sample as described above, it is possible to select and use the plunger pump with the suitable cylinder capacity to conditions, such as the amount of the sample to be injected into the liquid chromatograph. As a result, it is possible to obtain linearity accuracy of metering from small-amount injection to large-amount injection.

A preferred example of each of the plunger pumps used in the invention includes: a pump chamber; an intake port communicating with the pump chamber; a discharge port communicating with the pump chamber; a plunger having a tip end portion inserted into the pump chamber and for sliding on a straight line in a forward direction and a backward direction with respect to the pump chamber; a plunger body having a tip end portion fixed to a base end portion of the plunger and a threaded portion on an inner peripheral face of its base end portion; and a rotary driving portion having, on its outer peripheral face, a threaded portion to be engaged by screwing with the threaded portion and for being driven for rotation to thereby move, through the plunger body, the plunger along the straight line.

Although materials of the plunger pump are not specifically limited, in a preferred example, the threaded portion of the plunger body is made of polyphenylene sulfide resin and the threaded portion of the rotary driving portion is made of stainless steel. It is especially preferred that these materials of the portions to be engaged by screwing are selected preferably in the second plunger pump with the larger cylinder capacity.

Another preferable example of each of the plunger pumps used in the invention has a small clearance between the plunger pump and an inner wall of the pump chamber so as to be able to practice, in discharging after taking a solution into the pump chamber, a first and a second discharging manners. In the first discharging manner, an intake port side is closed, a discharge port side is opened, and the solution is discharged from the discharge port. In the second discharging manner, the intake port side is opened, the discharge port side is closed, and the solution in the pump chamber is discharged from the intake port through the clearance between the plunger and the inner wall of the pump chamber.

DETAILED DESCRIPTION OF THE INVENTION

Figure 1:
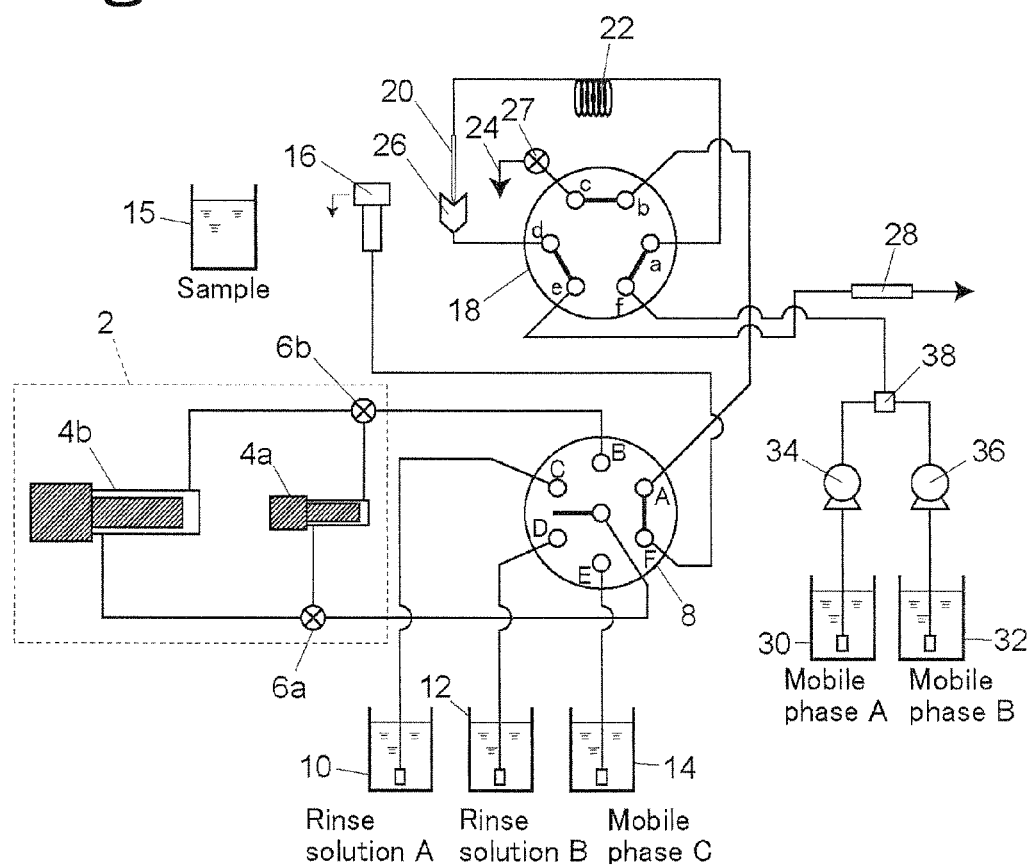
FIG. 1 is a flow path block diagram schematically showing a structure of an automatic sampler in an embodiment with a liquid chromatograph.

An embodiment of an automatic sampler will be described by using FIG. 1.

A pump portion 2 for taking in and discharging solutions has two plunger pumps including a first plunger pump 4a and a second plunger pump 4b. Both the plunger pumps 4a and 4b have different cylinder capacities and different solution intake and discharge amounts per stroke of the plungers. The second plunger pump 4b has a larger cylinder capacity than the first plunger pump 4a. For example, the cylinder capacity of the first plunger pump 4a is 100 μL, and the cylinder capacity of the second plunger pump 4b is 400 μL.

Both the plunger pumps 4a and 4b are connected to a first switching valve 8. Besides a common port connected to intake ports of the plunger pumps 4a and 4b, the first switching valve 8 includes a port "A" connected to a port "b" of a second switching valve 18, a port "B" connected to discharge ports of the plunger pumps 4a and 4b, ports "C" to "E" respectively connected to a vessel 10 containing a rinse solution A, a vessel 12 containing a rinse solution B, and a vessel 14 containing a mobile phase C, and a port "F" connected to a cleaning port 16. In the first switching valve 8, the common port can be connected to any one of the ports "A" to "F" and a pair of adjacent ones of the ports "A" to "F" can be connected at different times from the connection to the common port.

The intake ports of the plunger pumps 4a and 4b are connected in parallel to the common port of the first switching valve 8 with a three-way valve 6a interposed therebetween. The three-way valve 6a switches between connection of any one of the intake ports of the plunger pump 4a and plunger pump 4b and connection of the other to the common port of the first switching valve 8. The discharge ports of the plunger pumps 4a and 4b are connected in parallel to the port "B" of the first switching valve 8 with a three-way valve 6b interposed therebetween. The three-way valve 6b switches between connection of any one of the discharge ports of the plunger pumps 4a and 4b and connection of the other to the port "B" of the first switching valve 8. The three-way valves 6a and 6b form a pump selecting mechanism.

The second switching valve 18 includes a port "a" connected to a needle 20, a port "b" connected to the port "A" of the first switching valve 8, a port "c" connected to a drain flow path 24, a port "d" connected to an injection port 26, and ports "e" and "f" connected to flow paths forming an analytical flow path of the liquid chromatograph. The second switching valve 18 switches connection between adjacent ports. To put it concretely, the second switching valve 18 switches between a state in which the ports "a" and "b", "c" and "d", and "e" and "f" are connected, respectively, and a state in which the ports "b" and "c", "d" and "e", and "a" and "f" are connected, respectively. FIG. 1 shows the state in which the ports "b" and "c", "d" and "e", and "a" and "f" are connected.

The needle 20 is driven by a needle driving portion (not shown) and can move between a position of a sample vessel 15, a position of the cleaning port 16, and a position of the injection port 26. On a flow path connecting the port a of the second switching valve 18 and the needle 20, a sample loop 22 in which the solution taken in from a tip end of the needle 20 stays is provided.

A drain flow path 24 is a flow path for discharging the solution in the flow path of the automatic sampler to the outside and is opened and closed by a drain valve 27.

Flow paths connected to the port f of the second switching valve 18 are flow paths for pumping up respective mobile phases with solution sending pumps 34 and 36 from vessels 30, 32 containing the different mobile phases from each other and for mixing them with a mixer 38 and sending the solution. A flow path connected to the port "e" of the second switching valve 18 is a flow path having an analytical column 28.

The first switching valve 8 and the second switching valve 18 form a flow path switching mechanism.

Operation of the automatic sampler in the embodiment will be described by using FIGS. 2 to 6.

Figure 2:
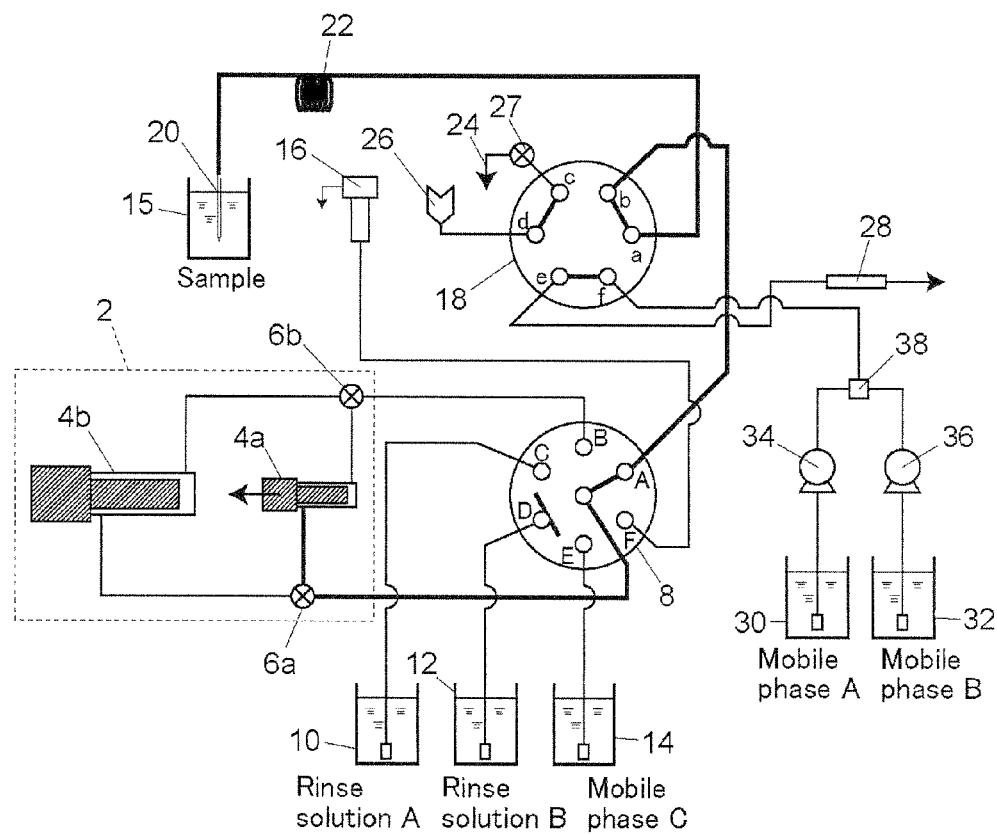
FIG. 2 is a flow path block diagram showing a state at the time of intake of a sample in the embodiment.

A flow path shown in a heavy line in FIG. 2 is a flow path formed at the time of intake of the sample. The flow path is formed when the common port and the port "A" are connected in the first switching valve 8 and the ports "a" and "b", "c" and "d", and "e" and "f" are connected, respectively, in the second switching valve 18. The needle 20 is inserted into the sample vessel 15 and a predetermined amount of the sample is taken in from the tip end of the needle 20 by driving the plunger pump 4a for the intake. In the pump portion 2, only one of the plunger pumps 4a and 4b is used. Which plunger pump is used is determined according to an intake amount of the solution such as the sample. The drawing shows a state in which the plunger pump 4a having the smaller capacity is used. The sample taken in from the tip end of the needle 20 stays in the sample loop 22.

Figure 3:
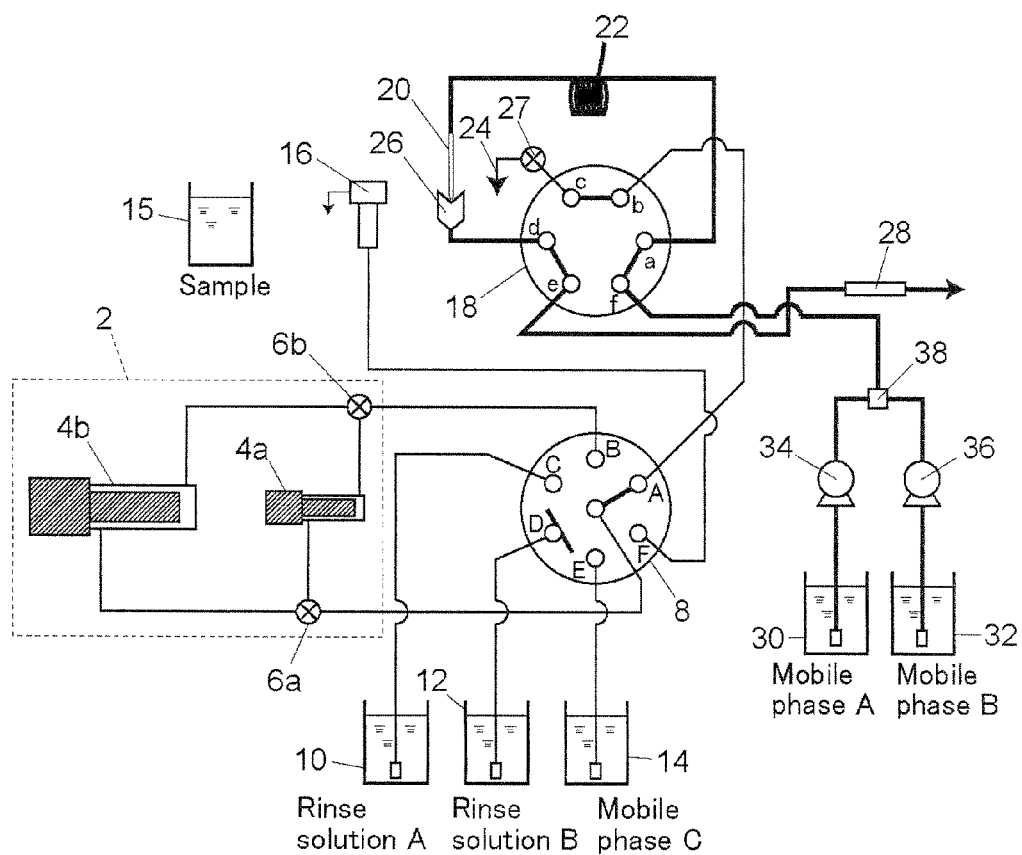
FIG. 3 is a flow path block diagram showing a state at the time of introduction of the sample into a liquid chromatograph in the embodiment.

A flow path shown in a heavy line in FIG. 3 is a flow path formed in introducing the sample staying in the sample loop 22 into the liquid chromatograph. This flow path is formed when the needle 20 is inserted into the injection port 26, the ports "b" and "c", "d" and "e", and "a" and "f" are connected, respectively, in the second switching valve 18. By forming this flow path and sending the mobile phases A and B by the solution sending pumps 34 and 36, the mobile phases mixed by the mixer 38 carry the sample staying in the sample loop 22 to the column 28, and the sample is separated into respective components.

In a gradient analysis, a ratio between the mobiles phases A and B is changed over time.

Figure 4:
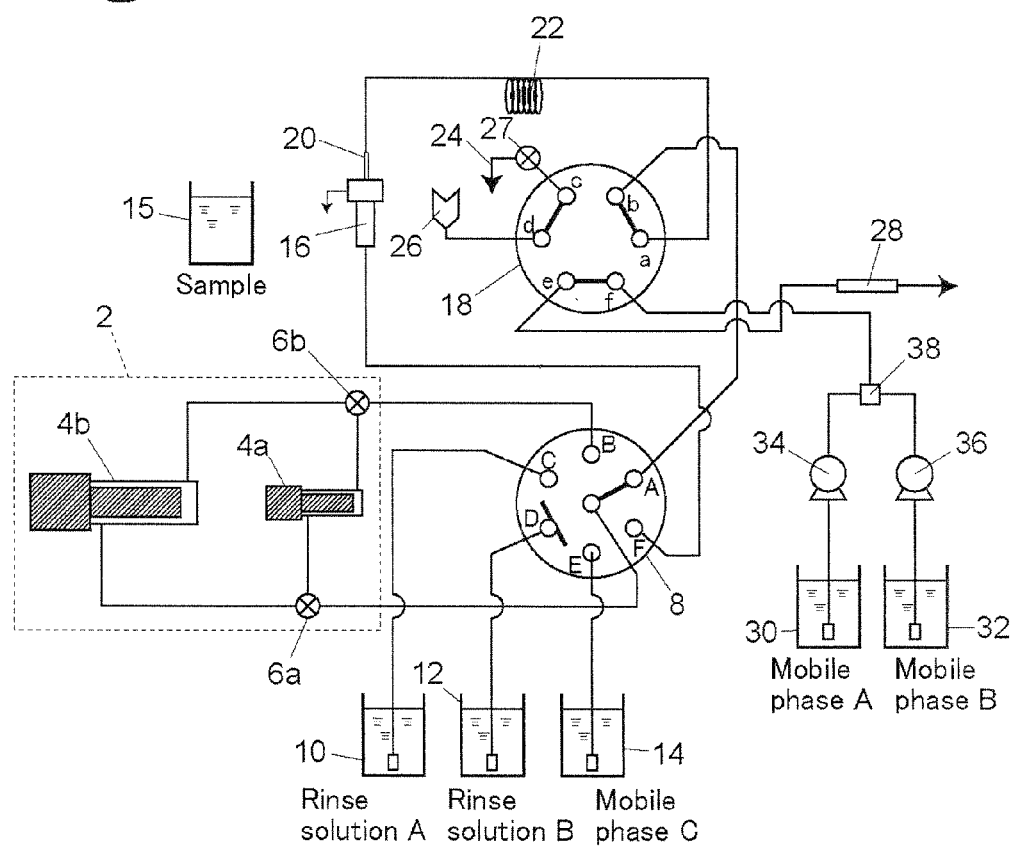
FIG. 4 is a flow path block diagram showing a state at the time of cleaning of a needle in the embodiment

FIG. 4 shows an example of a structure of a flow path at the time of cleaning of the needle 20. The needle 20 is inserted into the cleaning port 16, which is filled in advance with the rinse solution during an analysis time immediately before the cleaning. To fill the cleaning port 16 with the rinse solution, the rinse solution can be taken in by the plunger pump 4a having the smaller capacity. However, because an amount of the rinse solution to be supplied to the cleaning port 16 is larger than an amount of the sample to be injected into the liquid chromatograph, and it is not necessary to meter the rinse solution to be supplied to the cleaning port 16 with high accuracy, it is preferable to use the second plunger pump 4b having the larger capacity and capable of discharging a larger amount of rinse solution per stroke of the plunger. By using the second plunger pump 4b with the larger cylinder capacity to take in and discharge the rinse solution, it is possible to supply the rinse solution more quickly as compared with a case in which the first plunger pump 4a with the smaller cylinder capacity is used.

After the cleaning of the needle 20, the rinse solution in the cleaning port 16 is replaced. To replace the rinse solution in the cleaning port 16, first, as shown in a heavy line in FIG. 5, the common port of the first switching valve 8 is connected to the port "D", and the rinse solution is taken in by the second plunger pump 4b. Next, as shown in a heavy line in FIG. 6, the central common port and the port "F" are connected in the first switching valve 8 and the ports "b" and "c", "d" and "e", and "a" and "f" are connected, respectively, in the second switching valve 18. By driving the plunger pump 4b for discharge in this state, the rinse solution taken into the plunger pump 4b is discharged from a solution inlet side of the plunger pump 4b, the rinse solution discharged from the plunger pump 4b is sent into the cleaning port 16, the rinse solution overflowing the cleaning port 16 is discharged outside the cleaning port 16 as drainage, and the rinse solution in the cleaning port 16 is replaced.

Here, a small clearance exists between the plunger and a pump chamber inner wall in each of the plunger pumps 4a and 4b, and the taken-in solution is discharged from the solution inlet side through the clearance by driving the plunger for discharge with the solution outlet side closed.

Figure 5:
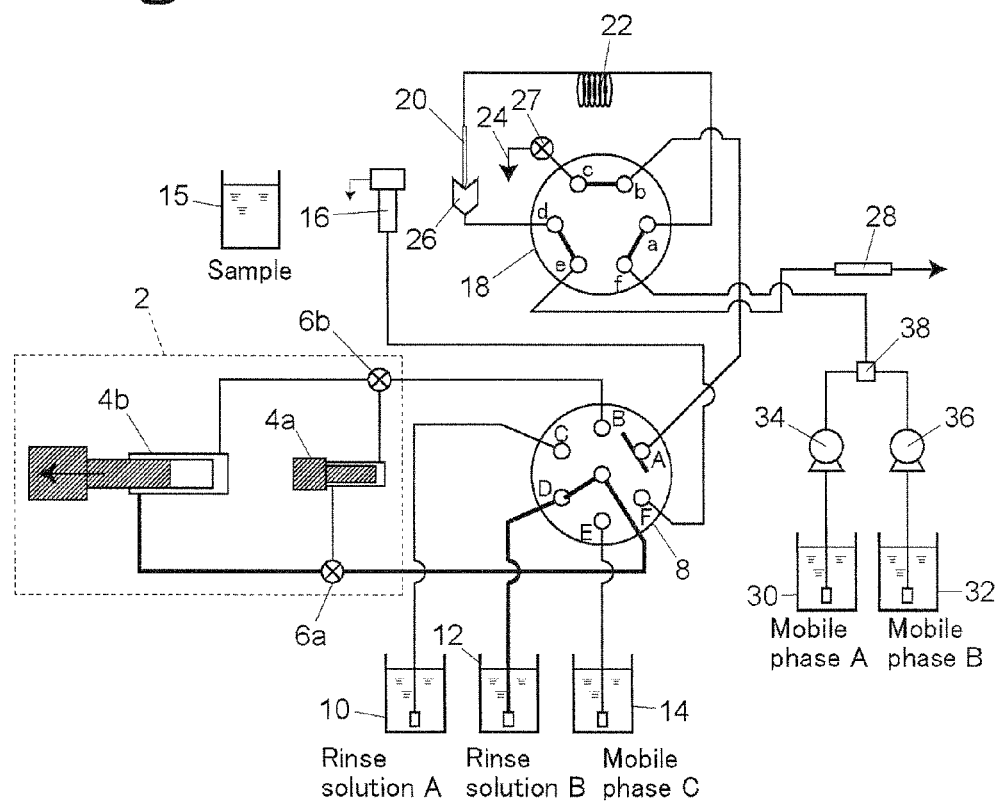
FIG. 5 is a flow path block diagram showing a state at the time of intake of a rinse solution in the embodiment.
Figure 6:
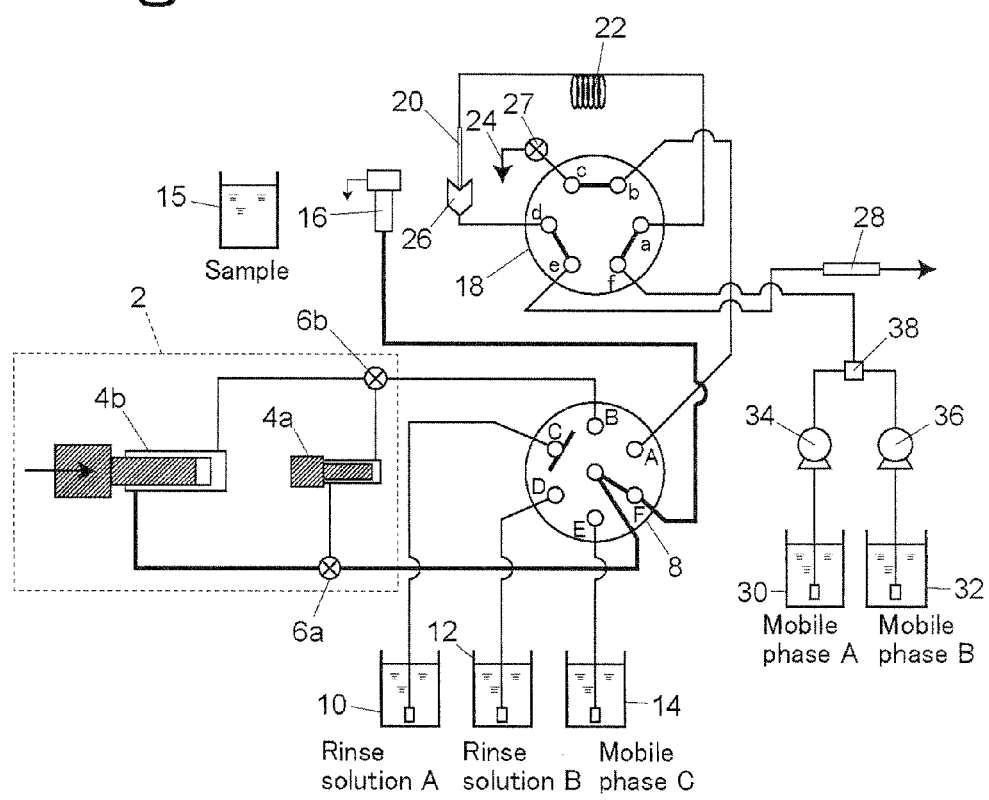
FIG. 6 is a flow path block diagram showing a state at the time of addition of the rinse solution to a cleaning port in the embodiment.
Figure 7:
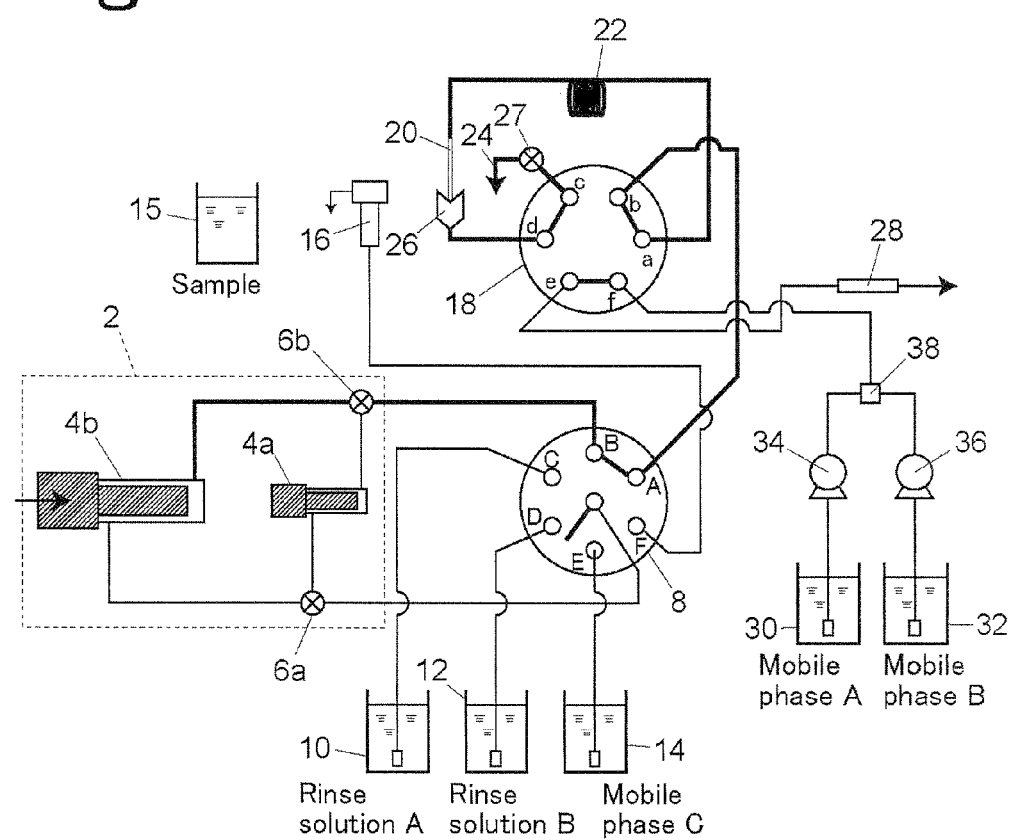
FIG. 7 is a flow path block diagram showing a state at the time of passage of the rinse solution through flow paths in the needle, a sample loop, and switching valves in the embodiment.

Cleaning of the flow paths in the needle 20, the sample loop 22, and the second switching valve 18 with the rinse solution is carried out by forming a flow path similar to that in FIG. 5, taking the rinse solution A or the rinse solution B into the plunger pump 4b, and passing the taken-in rinse solution through the flow paths in the needle 20, the sample loop 22, and the second switching valve 18. During the passage of the rinse solution through the flow paths in the needle 20, the sample loop 22, and the second switching valve 18, the needle 20 is inserted into the injection port 26, the ports "A" and "B" are connected in the first switching valve 8, and the ports a and "b", "c" and "d", and "e" and "f" are connected, respectively, in the second switching valve 18 as shown in a heavy line in FIG. 7. By opening the drain valve 27 and driving the plunger pump 4b for discharge in this state, the flow paths in the needle 20, the sample loop 22, and the second switching valve 18 are cleaned while discharging the rinse solution from the drain flow path 24. Because the plunger pump 4b is used for supplying the rinse solution to the flow paths in the needle 20, the sample loop 22, and the second switching valve 18, discharge speed of the rinse solution is higher than that of when the plunger pump 4a is used and cleaning effect in the flow paths increases.

The cleaning operation of the flow paths in the needle 20, the sample loop 22, and the second switching valve 18 can be carried out not only when the analysis is not being carried out but also after the injection of the sample and before the next sample intake operation during the analysis time. In this case, the rinse solution A or the rinse solution B which is a different solvent from the mobile phase for the analysis remains in the flow paths in the needle 20, the sample loop 22, and the second switching valve 18 and, if the analysis is started in this state, a baseline of a chromatogram may become unstable in some cases. Therefore, a mobile phase C having the same composition as the mobile phase for the analysis is sent into the flow paths in the needle 20, the sample loop 22, and the second switching valve 18 to carry out replacement of the solvent. In the case of the gradient analysis, the composition of the mobile phase C is conformed to that in an early stage of a gradient. In this way, it is possible to keep a baseline of the chromatogram stable in a next analysis after cleaning of the flow paths in the needle 20, the sample loop 22, and the second switching valve 18.

Figure 8:
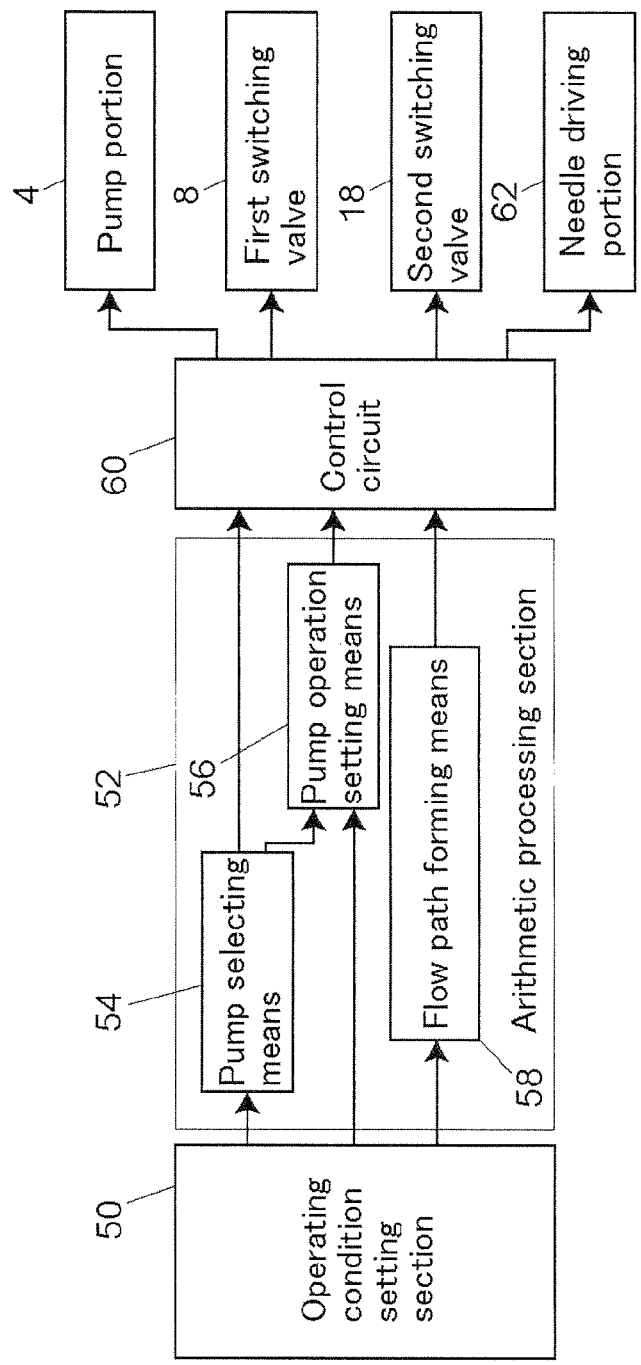
FIG. 8 is a block diagram schematically showing a control system in the embodiment.

The control system of the automatic sampler in the embodiment will be described by using FIG. 8.

The pump portion 2, the first switching valve 8, the second switching valve 18, and a needle driving portion 62 are respectively controlled by signals provided by a control circuit 60. The control circuit 60 is for generating the signals based on commands from an arithmetic processing section 52. The arithmetic processing section 52 sets operating conditions of the automatic sampler according to analysis conditions set by an analyst. The arithmetic processing section 52 includes a pump selecting means 54, a pump operation setting means 56, and a flow path forming means 58.

The pump selecting means 54 selects which of the plunger pumps 4a and 4b to use according to an intake amount of the sample and a step to be carried out and controls the three-way valve 6a or 6b so that the selected plunger pump becomes usable. As an example of the pump selecting means 54, it is formed to select the first plunger pump 4a with the smaller capacity when the amount of the sample to be injected into the liquid chromatograph and set by the operating condition setting section 50 is a certain amount or smaller and select the second plunger pump 4b with the larger capacity when the amount of the sample to be injected is larger than the certain amount or for supplying the rinse solution. For example, if the cylinder capacity of the plunger pump 4a is 100 μL and the cylinder capacity of the plunger pump 4b is 400 μL, the plunger pump 4a is used when the intake amount of the sample is 100 μL or smaller and the plunger pump 4b is used when the intake amount of the sample is larger than 100 μL or for supplying the rinse solution.

The pump operation setting means 56 is formed to drive the plunger pump 4a or 4b selected by the pump selecting means 54 based on the operating conditions from the operating condition setting section 50. The flow path forming means 58 is formed to form a flow path for carrying out a sample intake step, a step of introducing the sample into the liquid chromatograph, a step of cleaning the needle 20, a step of discharging the rinse solution from the cleaning port 16, or a rinse solution addition step and to control operations of the first switching valve 8, the second switching valve 18, and the needle driving portion 62. This control system is implemented via a computer for controlling operation of the automatic sampler.

Figure 9:
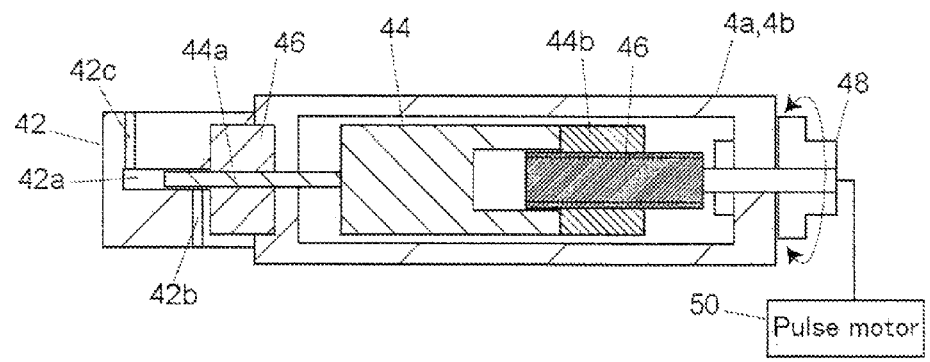
FIG. 9 is a sectional view of an example of a structure of a plunger pump.
Figure 10:
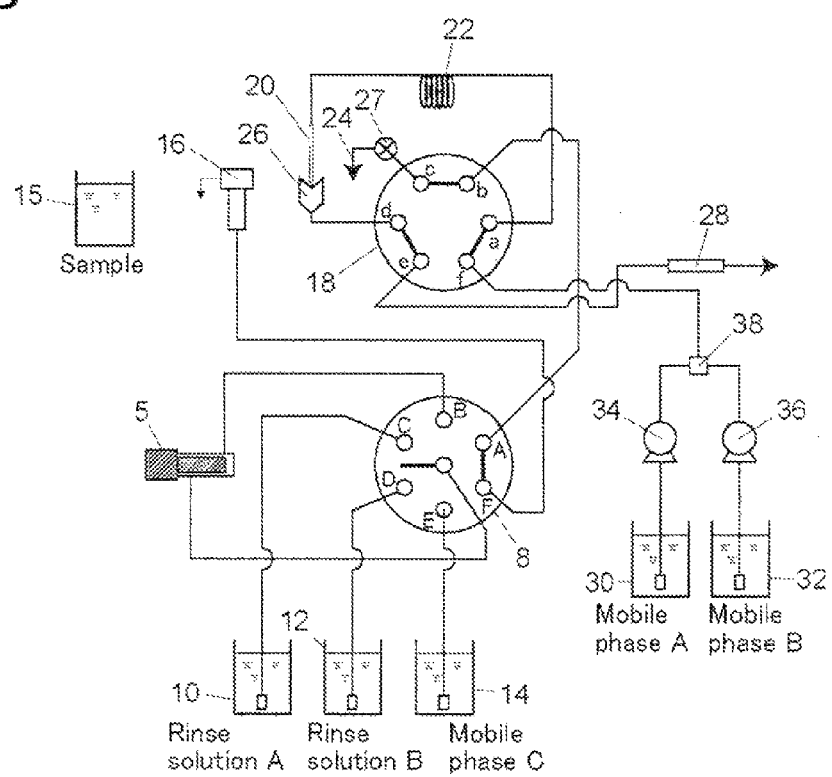
FIG. 10 is a flow path block diagram schematically showing an example of a prior-art automatic sampler with a liquid chromatograph.

FIG. 9 is a sectional view of an example of a structure of each of the plunger pumps 4a and 4b of the pump portion 2. The plunger pumps 4a and 4b have the same structures except that they have the different cylinder capacities. Each of the plunger pumps 4a and 4b includes a pump chamber 42a, an intake port 42b, and a discharge port 42c in a pump head 42 provided at a tip end of the pump. A plunger 44a is inserted into the pump chamber 42a through a seal 46. The plunger 44a has a base end portion fixed to a tip end of a plunger body 44 and slides in the pump chamber 42a as the plunger body 44 reciprocates. A base end portion of the plunger body 44 is formed as a threaded portion 44b having a threaded inner peripheral face and is engaged by screwing with a rotary driving portion 46 having a threaded outer peripheral face. The rotary driving portion 46 is driven for rotation as a pulley 48 rotates and the pulley 48 is driven for rotation by a pulse motor 50.

In such a plunger pump, high loads are applied on the engaged portion between the threaded portion 44b and the rotary driving portion 46 when solution sending pressure is high. Especially on the plunger pump 4b having the larger cylinder capacity, the larger load is applied, and therefore, the engaged portion of the plunger pump 4b needs to be made of material that can bear such a load. An example of material of the threaded portion 44b is PPS (polyphenylene sulfide) resin, and an example of material of the rotary driving portion 46 is stainless steel (SUS303).

The small clearance exists between the plunger 44a and an inner wall of the pump chamber 42a in each of the plunger pumps 4a and 4b. To take the solution into the pump chamber 42a, the intake port 42b side is opened, the discharge port 42c side is closed, and the plunger 44a is driven for intake. After taking the solution into the pump chamber 42a, the plunger 44a is driven for discharge to discharge the solution from the pump chamber 42a. There are two discharging methods. The first discharging method is to close the intake port 42b side and open the discharge port 42c side, and the solution is discharged from the discharge port 42c. The second discharging method is to open the intake port 42b and close the discharge port 42c side. By this method, the solution in the pump chamber 42a is discharged from the intake port 42b through the clearance between the plunger 44a and the pump chamber 42a.

What is claimed is:

1. An automatic sampler for a liquid chromatograph and for injecting a taken-in sample into an analytical flow path of the liquid chromatograph, the automatic sampler comprising:
   a first plunger pump for taking in the sample;
   a second plunger pump for taking in the sample and having a larger cylinder capacity than the first plunger pump;
   a sample loop for temporarily retaining the sample taken in by the first or second plunger pump;
   a flow path switching mechanism including a switching valve and for switching, by switching of the switching valve, between a flow path for taking the sample into the sample loop with the first or second plunger pump and a flow path for supplying the sample taken into and retained by the sample loop to an analytical flow path of the liquid chromatograph with a mobile phase;
   a pump selecting mechanism disposed between intake ports and discharge ports of both the plunger pumps and the flow path switching mechanism, and for switching connection with the flow path switching mechanism so as to selectively connect one of the plunger pumps to the flow path switching mechanism, and
   a pump selecting means for switching the pump selecting mechanism so that the pump selecting mechanism selects the first plunger pump when an amount of the sample to be injected into the analytical flow path of the liquid chromatograph is a predetermined amount or smaller and selects the second plunger pump when the injected amount of the sample is larger than the predetermined amount.

2. The automatic sampler according to claim 1,
wherein each of the plunger pumps includes:
a pump chamber;
an intake port communicating with the pump chamber; a discharge port communicating with the pump chamber;
a plunger having a tip end portion inserted into the pump chamber and for sliding on a straight line in a forward direction and a backward direction with respect to the pump chamber;
a plunger body having a tip end portion fixed to a base end portion of the plunger and a threaded portion on an inner peripheral face of its base end portion; and
a rotary driving portion having, on its outer peripheral face, a threaded portion to be engaged by screwing with the threaded portion and for being driven for rotation to thereby move, through the plunger body, the plunger along the straight line.

3. The automatic sampler according to claim 2,
wherein the threaded portion of the plunger body of the plunger pump is made of polyphenylene sulfide resin and the threaded portion of the rotary driving portion is made of stainless steel.

4. The automatic sampler according to claim 3,
wherein the plunger pump having a combination of the threaded portion made of polyphenylene sulfide resin and the threaded portion made of stainless steel is the second plunger pump.

5. The automatic sampler according to claim 3,
wherein the plunger pump having a combination of the threaded portion made of polyphenylene sulfide resin and the threaded portion made of stainless steel is each of the plunger pumps.

6. The automatic sampler according to claim 2,
wherein, each of the plunger pumps has a small clearance between the plunger pump and an inner wall of the pump chamber so as to be able to practice, in discharging after taking a solution into the pump chamber, a first and a second discharging manner, the first discharging manner being a manner in which an intake port side is closed, a discharge port side is opened, and the solution is discharged from the discharge port, and the second discharging manner being a manner in which the intake port side is opened, the discharge port side is closed, and the solution in the pump chamber is discharged from the intake port through the clearance between the plunger and the inner wall of the pump chamber.

* * * * *